United States Patent [19]
Heimberger et al.

[11] Patent Number: 5,554,099
[45] Date of Patent: Sep. 10, 1996

[54] ENDOSCOPIC INSTRUMENT

[75] Inventors: Rudolf Heimberger, Oberderdingen; Uwe Schaumann, Knittlingen, both of Germany

[73] Assignee: Richard Wolf GmbH, Knittlingen, Germany

[21] Appl. No.: 346,443

[22] Filed: Nov. 29, 1994

[30] Foreign Application Priority Data

Dec. 2, 1993 [DE] Germany .......................... 43 41 062.6

[51] Int. Cl.⁶ ..................................... A61B 1/06
[52] U.S. Cl. ........................................... 600/160; 600/161
[58] Field of Search .................................. 600/160, 161, 600/920; 351/166

[56] References Cited

U.S. PATENT DOCUMENTS 4,445,892  5/1984  Hussein et al. ...................... 604/101
4,624,243  11/1988  Lowery et al. ............... 128/6
5,335,647  8/1994  Brustad .............................. 600/920 X

FOREIGN PATENT DOCUMENTS 2814236  11/1978  Germany .
3428645  2/1985  Germany .

OTHER PUBLICATIONS

Applied Optics, vol. 24, No. 14, 15. Feb. 1985, pp. 508–512.

*Primary Examiner*—Lynne A. Reichard
*Assistant Examiner*—Beverly M. Flanagan
*Attorney, Agent, or Firm*—Panitch Schwarze Jacobs & Nadel, P.C.

[57] ABSTRACT

The endoscopic instrument has a long, stretched out shaft (5) and at least one rod-shaped lens (6) arranged therein. The rod lens (6) is provided on its peripheral surfaces (10) with a coating that increases the breaking strength. The coating may be, for example, polyimide, amorphous carbon, or silicon-oxide carbide. To increase adhesion of the coating the rod lens may be pretreated with caustic on its peripheral surfaces.

5 Claims, 1 Drawing Sheet

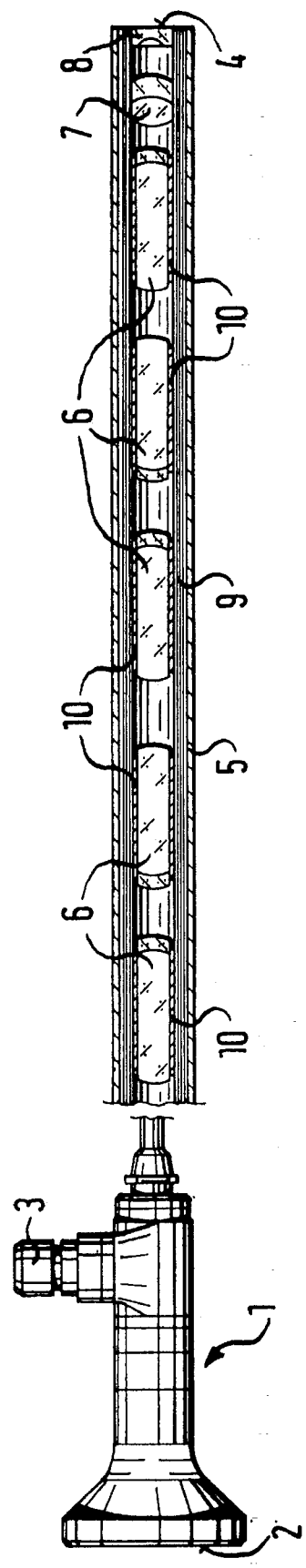

ENDOSCOPIC INSTRUMENT

FIELD OF THE INVENTION

The invention pertains to an endoscopic instrument with a long stretched-out shaft having at least one rod-shaped lens arranged therein.

BACKGROUND OF THE INVENTION

Endoscopic instruments are presently used in many fields of medicine, but they are also used in engineering, where they are known as so-called technoscopes. In recent years, a large number of applications have been made possible only as a result of the fact that significant progress has been made in endoscopic technology. Thus, there are already endoscopes known today that have diameters that amount to only a few millimeters in order to be able to penetrate even the smallest clearances.

Rod lenses are often used in long, stretched out, thin endoscopes of this type. Such rod lenses can have a diameter of 2.78 mm, for example, with a total length of 28 mm. They sit inside a tubular shaft, wherein the shaft is, of course, kept as thin as possible and only as thick as necessary in terms of its wall thickness in order to keep the overall cross-sectional dimensions as small as possible.

With such endoscopes, it is hardly possible to avoid the fact that, in spite of the protected position of the rod lenses within the shaft, when the shaft bends, forces act upon these rod lenses as well. In practice, it is thus not possible to avoid the fact that the optic that lies inside the shaft, a rod lens in particular, is placed under stress by external bending loads and can possibly be damaged in this way. If such a lens breaks, it destroys the complete endoscope. Because of this, in practice, there are limits to the development of endoscope optics with external dimensions that are as small as possible.

SUMMARY OF THE INVENTION

The present invention performs the task of configuring a generic endoscope in such a way, that a higher breaking strength of the rod lens or rod lenses that are found in them is ensured in order to thus increase the sturdiness of the endoscopic instrument, as well as to be able to further reduce the size with respect to cross-sectional dimensions.

In accordance with the invention, this object is achieved by means of the rod lens or the rod lenses being provided on their peripheral surfaces with a coating that increases the breaking strength. A coating of this type increases the diameter of the rod lens only insignificantly, but in contrast, increases the breaking strength substantially. The invention suggests coatings that are suitable for such types of rod lenses and that can be applied reliably and inexpensively.

In order to ensure good adhesion of the coating to the rod lens on the one hand, and to further increase the breaking strength of the rod lens on the other, it is beneficial if the lens or the lenses are subjected to a caustic treatment before the coating. As a rule, the caustic treatment takes place by means of a chemical that is corrosive to the lens material. In the case of glass or glass-like materials, for example, this can be done by means of hydrofluoric acid. It goes without saying, that all of the treatments of the lens, in accordance with the present invention, must at least take place in the area of the peripheral surfaces of the lens, and to the extent that it is beneficial or at least not a hindrance, they can, if necessary, be carried out in the area of the lens faces as well.

Polyimide coating represents a coating that is especially simple and thus inexpensive. A plastic coating of such a type on the rod lens can be carried out by simple immersion, or even by spraying, in which case the thickness of the coating can be adjusted almost at will by means of repetition of the procedure.

An especially hard coating can be produced by the application of an amorphous carbon coating (diamond coat). Coatings of this type can be applied in a known manner by means of a CVD (chemical vapor deposition) process.

If the coating is supposed to withstand high thermal loads as well, then a silicon-oxide carbide coating is to be recommended, which can also be applied by means of the CVD process. As an alternative, PVD (physical vapor deposition) coatings can also be provided, depending in each case on the additional characteristics that the rod lenses are to have along with the increased breaking strength.

BRIEF DESCRIPTION OF THE DRAWING

The foregoing summary, as well as the following detailed description of a preferred embodiment of the invention, will be better understood when read in conjunction with the appended drawing which shows further features and advantages of the invention. For the purpose of illustrating the invention, there is shown in the drawing an embodiment which is presently preferred. It should be understood, however, that the invention is not limited to the precise arrangements and instrumentalities shown. In the drawing:

The sole figure shows an endoscope according to the invention in side view with a shaft that is represented in an enlarged longitudinal section.

DETAILED DESCRIPTION OF THE PREFERRED EMBODIMENT

The endoscope shown has a proximal part 1 with eyepiece 2, as well as a laterally leading fiber optic light guide connection 3. The long, stretched out cylindrical shaft 5, which extends to the distal end 4, is formed by a metal tube. Residing centrally within this shaft are a total of five rod lenses 6, one lens pair 7, and a distal lens 8 that is configured as a terminating window. The lenses 6 through 8 are surrounded inside the shaft by light guides 9, which are a part of the illumination optics and which are supplied by means of the fiber optic light guide connection 3. They terminate at the distal shaft end 4, together with the shaft and the distal terminating window 8.

The rod lenses 6 have on their peripheral surfaces 10 the coating that was described earlier, by means of which the breaking strength of the lenses 10 is significantly increased. In the case of the embodiment shown, the rod lenses 6 are coated on their peripheral sides with polyimide. In this way, the breaking strength is significantly increased in the critical area transverse to the longitudinal axis of the lenses 6, so that during bending loads on the shaft 5, which are common in endoscopic use, and in spite of the very slight diameter of the rod lenses 6, damage or breakage of these does not occur.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

We claim:

1. Endoscopic instrument with a long, stretched out shaft (5), and with at least one rod-shaped lens (6) arranged therein, characterized in that the lens (6) is provided on its peripheral surfaces (10) with a coating that increases its breaking strength.

2. Endoscopic instrument according to claim 1, wherein the lens (6) is subjected to a caustic treatment, at least on its peripheral surfaces, before being coated.

3. Endoscopic instrument according to claim 1, wherein the coating comprises polyimide.

4. Endoscopic instrument according to claim 1, wherein the coating comprises amorphous carbon.

5. Endoscopic instrument according to claim 1, wherein the coating comprises silicon-oxide carbide.

* * * * *